United States Patent [19]

Ermann

[11] Patent Number: 4,871,841
[45] Date of Patent: Oct. 3, 1989

[54] 2-OXO-1-[[(SUBSTITUTED SULFONYL)AMINO]-CARBONYL]AZETIDINES

[75] Inventor: Peter H. Ermann, Donaustauf, Fed. Rep. of Germany

[73] Assignee: E. R. Squibb & Sons, Inc., Princeton, N.J.

[21] Appl. No.: 137,265

[22] Filed: Dec. 23, 1987

[51] Int. Cl.$^4$ ................. C07D 403/12; C07D 401/14; C07D 417/14; A61K 31/505
[52] U.S. Cl. ................................. 540/363; 540/357; 540/360; 540/364
[58] Field of Search ............... 540/355, 363, 364, 357, 540/360

[56] References Cited

U.S. PATENT DOCUMENTS 4,587,047  5/1986  Breuer et al. ................. 540/363
4,743,685  5/1988  Breuer ............................ 540/363

FOREIGN PATENT DOCUMENTS 2181130  4/1987  United Kingdom .

Primary Examiner—Mark L. Berch
Attorney, Agent, or Firm—Gaul Timothy J.; Donald J. Barrack

[57]  ABSTRACT

Antibacterial activity is exhibited by 2-azetidinones having a 3-acylamino substituent and having an activating group in the 1-position of the formula

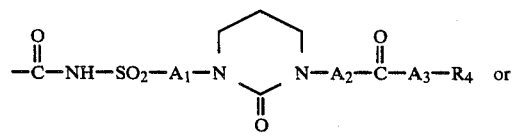

or -continued

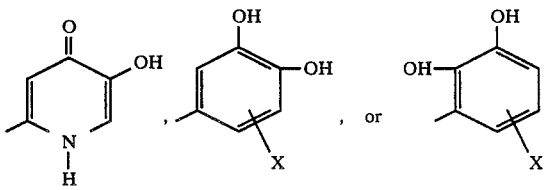

wherein $R_4$ is

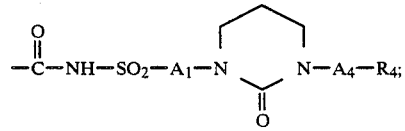

wherein $A_1$ is a single bond,

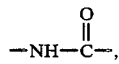

—NH— or

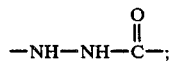

$A_2$ is a single bond, —NH—, —CH$_2$—CH$_2$—NH— or

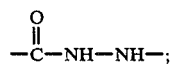

$A_3$ is a single bond, —CH=CH—, —(CH$_2$)$_t$—, —NH—(CH$_2$)$_p$— or

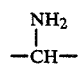

wherein t is 1, 2, 3 or 4 and p is 0 or 1; and $A_4$ is a single bond —CH$_2$—, —NH—CH$_2$—, or —N=CH—.

12 Claims, No Drawings

2-OXO-1-[[(SUBSTITUTED SULFONYL)AMINO]-CARBONYL]AZETIDINES

BRIEF DESCRIPTION OF THE INVENTION

Compounds having the formula

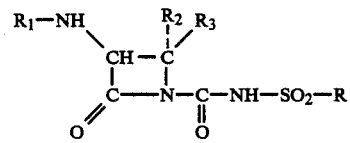   I and pharmaceutically acceptable salts thereof, exhibit antibacterial activity. In formula I, and throughout the specification, the symbols are as defined below.

R is

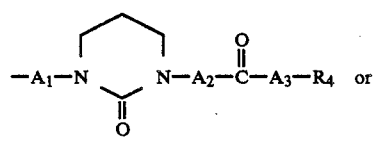 or

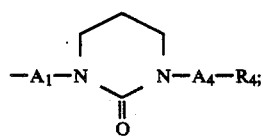

$R_1$ is an acyl group derived from a carboxylic acid;

$R_2$ and $R_3$ are the same or different and each is hydrogen, alkyl, alkenyl, alkynyl, cycloalkyl, phenyl, substituted phenyl or a 4, 5, 6 or 7-membered heterocycle (hereinafter referred to as $R_x$), or one of $R_2$ and $R_3$ is hydrogen and the other is azido, halomethyl, dihalomethyl, trihalomethyl, alkoxycarbonyl, 2-phenylethenyl, 2-phenylethynyl, carboxyl, —CH$_2$X$_1$ [wherein X$_1$ is azido, amino (—NH$_2$), hydroxy, carboxyl, alkoxycarbonyl, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano,

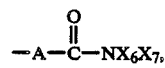

—S—X$_2$, or —O—X$_2$ (wherein A, X$_2$, X$_6$ and X$_7$ are as hereinafter defined)], —S—X$_2$ or —O—X$_2$ [wherein X$_2$ is alkyl, substituted alkyl, phenyl, substituted phenyl, phenylalkyl, (substituted phenyl)alkyl, alkanoyl, phenylalkanoyl, (substituted phenyl)alkanoyl, phenylcarbonyl, (substituted phenyl)carbonyl, or heteroarylcarbonyl],

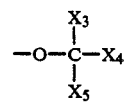

or

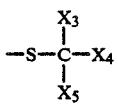

[wherein one of $X_3$ and $X_4$ is hydrogen and the other is hydrogen or alkyl, or $X_3$ and $X_4$ when taken together with the carbon atom to which they are attached form a cycloalkyl group; and $X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl

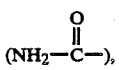

(substituted amino)carbonyl, or cyano (—C≡N)], or

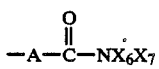

[wherein A is —CH=CH—, —(CH$_2$)$_m$—, —(CH$_2$)$_m$—O—, —(CH$_2$)$_m$—NH—, or —CH$_2$—S—CH$_2$—, m is 0, 1 or 2, and $X_6$ and $X_7$ are the same or different and each is hydrogen, alkyl, phenyl or substituted phenyl, or $X_6$ is hydrogen and $X_7$ is amino, substituted amino, alkanoylamino or alkoxy, or $X_6$ and $X_7$ when taken together with the nitrogen atom to which they are attached form a 4, 5, 6 or 7-membered heterocycle];

$R_4$ is

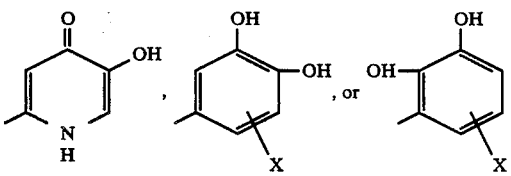

wherein X is hydrogen, halogen, carboxyl, sulfo (—SO$_3$H), carbamoyl, aminosulfonyl, cyano, alkyl, alkanoyl, or alkoxycarbonyl;

$A_1$ is a single bond,

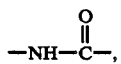

—NH— or

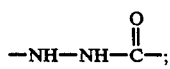

$A_2$ is a single bond, —NH—, —CH$_2$—CH$_2$—NH—, or

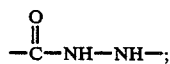

$A_3$ is a single bond, —CH=CH—, —(CH$_2$)$_r$—, —NH—(CH$_2$)$_p$— or

wherein t is 1, 2, 3 or 4 and p is 0 or 1; and

A₄ is a single bond, —CH₂—, —NH—CH₂—, or —N=CH—.

The above symbols (e.g., A₁, A₂, A₃ and A₄) are used to represent groups of multiple atoms. These groups are inserted in the structural formulas shown herein in the order in which they are presented (i.e., from left to right). For example, if the substituent "R" of a compound of formula I contains the group having the formula contains the group

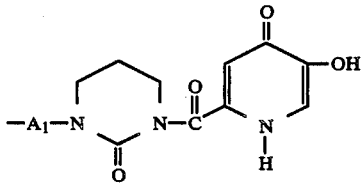

and
A₁ is

the group would be

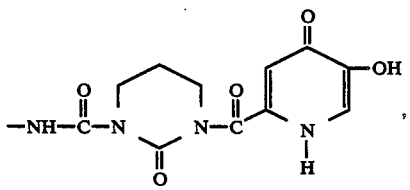

not

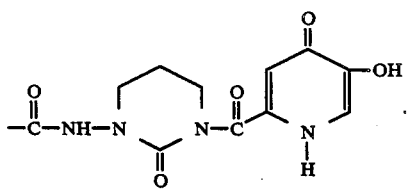

Listed below are definitions of various terms used to describe the β-lactams of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred.

The terms "cycloalkyl" and "cycloalkenyl" refer to cycloalkyl and cycloalkenyl groups having 3, 4, 5, 6 or 7 carbon atoms.

The term "substituted alkyl" refers to alkyl groups substituted with one or more (preferably 1, 2 or 3) azido, amino (—NH₂), halogen, hydroxy, carboxy, cyano, alkoxycarbonyl, aminocarbonyl, alkanoyloxy, alkoxy, phenyloxy, (substituted phenyl)oxy, mercapto, alkylthio, phenylthio, (substituted phenyl)thio, alkylsulfinyl, or alkylsulfonyl groups.

The terms "alkanoyl", "alkenyl", and "alkynyl" refer to both straight and branched chain groups. Those groups having 2 to 10 carbon atoms are preferred.

The terms "halogen" and "halo" refer to fluorine, chlorine, bromine and iodine.

The term "substituted phenyl" refers to a phenyl group substituted with 1, 2 or 3 amino (—NH₂), halogen, hydroxyl, trifluoromethyl, alkyl (of 1 to 4 carbon atoms), alkoxy (of 1 to 4 carbon atoms), alkanoyloxy, aminocarbonyl, or carboxy groups.

The expression "a 4, 5, 6 or 7-membered heterocycle" (referred to as "R_x") refers to substituted and unsubstituted, aromatic and non-aromatic groups containing one or more (preferably 1, 2 or 3) nitrogen, oxygen or sulfur atoms. Exemplary substituents are oxo (=O), halogen, hydroxy, nitro, amino, cyano, trifluoromethyl, alkyl of 1 to 4 carbons, alkoxy of 1 to 4 carbons, alkylsulfonyl, phenyl, substituted phenyl, 2-furfurylideneamino

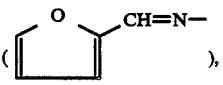

benzylideneamino and substituted alkyl groups (wherein the alkyl group has 1 to 4 carbons). One type of "4, 5, 6 or 7-membered heterocycle" is the "heteroaryl" group. The term "heteroaryl" refers to those 4, 5, 6 or 7-membered heterocycles which are aromatic. Exemplary heteroaryl groups are substituted and unsubstituted pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, and tetrazolyl. Exemplary nonaromatic heterocycles (i.e., fully or partially saturated heterocyclic groups) are substituted and unsubstituted azetidinyl, oxetanyl, thietanyl, piperidinyl, piperazinyl, imidazolidinyl, oxazolidinyl, pyrrolidinyl, tetrahydropyrimidinyl, dihydrothiazolyl and hexahydroazepinyl. Exemplary of the substituted 4, 5, 6 or 7-membered heterocycles are 1-alkyl-3-azetidinyl, 2-oxo-1-imidazolidinyl, 3-alkylsulfonyl-2-oxo-1-imidazolidinyl, 3-benzylideneamino-2-oxo-1-imidazolidinyl, 3-alkyl-2-oxo-1-imidazolidinyl, 3-phenyl (or substituted phenyl)-2-oxo-1-imidazolidinyl, 3-benzyl-2-oxo-1-imidazolidinyl, 3-(2-aminoethyl)-2-oxo-1-imidazolidinyl, 3-amino-2-oxo-1-imidazolidinyl, 3-[(alkoxycarbonyl)amino]-2-oxo-1-imidazolidinyl, 3-[2-[(alkoxycarbonyl)amino]ethyl]-2-oxo-1-imidazolidinyl, 2-oxo-1-pyrrolidinyl, 2-oxo-3-oxazolidinyl, 4-hydroxy-6-methyl-2-pyrimidinyl, 2-oxo-1-hexahydroazepinyl, 2-oxo-3-pyrrolidinyl, 2-oxo-3-tetrahyrofuranyl, 2,3-dioxo-1-piperazinyl, 2,5-dioxo-1-piperazinyl, 4-alkyl-2,3-dioxo-1-piperazinyl, and 4-phenyl-2,3-dioxo-1-piperazinyl.

The term "substituted amino" refers to a group having the formula —NX₈X₉ wherein X₈ is hydrogen, alkyl, phenyl, substituted phenyl, phenylalkyl or (substituted phenyl)alkyl, and X₉ is alkyl, phenyl, substituted phenyl, phenylalkyl, (substituted phenyl)alkyl, hydroxy, cyano, alkoxy, phenylalkoxy, or amino (—NH₂).

The term "acyl" refers to all organic radicals derived from an organic acid (i.e., a carboxylic acid) by removal of the hydroxyl group. Certain acyl groups are, of course, preferred but this preference should not be viewed as a limitation of the scope of this invention. Exemplary acyl groups are those acyl groups which have been used in the past to acylate, β-lactam antibiotics including 6-aminopenicillanic acid and derivatives and 7-aminocephalosporanic acid and derivatives; see, for example, *Cephalosporins and Penicillins,* edited by Flynn, Academic Press (1972), German Offenlegungsschrift No. 2,716,677, published Oct. 10, 1978, Belgian Pat. No. 867,994, published Dec. 11, 1978, U.S. Pat. No. 4,152,432, issued May 1, 1979, U.S. Pat. No. 3,971,778, issued July 27, 1976, U.S. Pat. No. 4,172,199, isued Oct. 23, 1979, and British Pat. No. 1,348,894, published Mar. 27, 1974. The portions of these references describing various acyl groups are incorporated herein by reference. The following list of acyl groups is presented to further exemplify the term "acyl"; it should not be regarded as limiting that term. Exemplary acyl groups are:

(a) Aliphatic groups having the formula

wherein $R_a$ is alkyl; cycloalkyl; alkoxy; alkenyl; cycloalkenyl; cyclohexadienyl; or alkyl or alkenyl substituted with one or more halogen, cyano, nitro, amino, mercapto, alkylthio, or cyanomethylthio groups.

(b) Carbocyclic aromatic groups having the formula

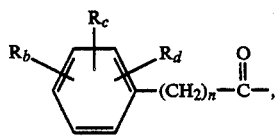

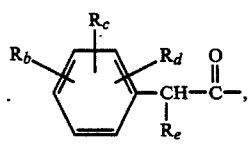

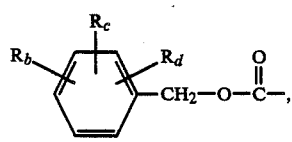

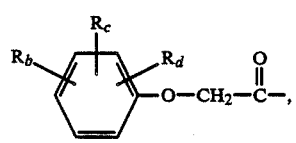

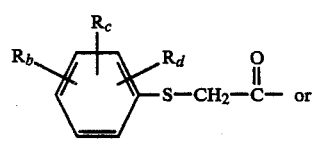

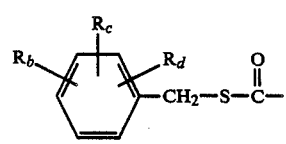

wherein n is 0, 1, 2 or 3; $R_b$, $R_c$, and $R_d$ each is independently hydrogen, halogen, hydroxyl, nitro, amino, cyano, trifluoromethyl, alkyl of 1 to 4 carbon atoms, alkoxy of 1 to 4 carbon atoms or aminomethyl; and $R_e$ is amino, hydroxyl, a carboxyl salt, protected carboxyl, formyloxy, a sulfo salt, a sulfoamino salt, azido, halogen, hydrazino, alkylhydrazino, phenylhydrazino, or [(alkylthio)thioxomethyl]thio.

Preferred carbocyclic aromatic acyl groups include those having the formula

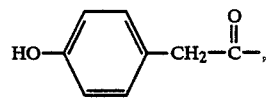

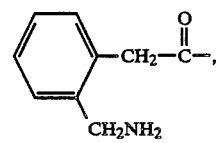

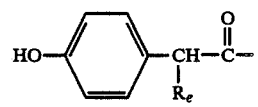

($R_e$ is preferably a carboxyl salt or sulfo salt) and

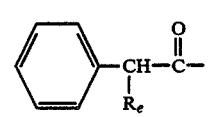

($R_e$ is preferably a carboxyl salt or sulfo salt).

(c) Heteroaromatic groups having the formula

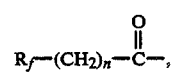

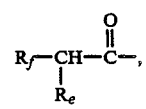

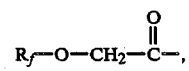

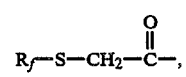

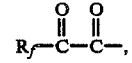

wherein n is 0, 1, 2 or 3; $R_e$ is as defined above; and $R_f$ is a substituted or unsubstituted 5-, 6- or 7-membered heterocyclic ring containing 1, 2, 3 or 4 (preferably 1 or 2) nitrogen, oxygen and sulfur atoms. Exemplary heterocyclic rings are thienyl, furyl, pyrrolyl, pyridinyl, pyrazolyl, pyrazinyl, thiazolyl, pyrimidinyl, thiadiazolyl and tetrazolyl. Exemplary substituents are halogen, hydroxyl, nitro, amino, protected amino, cyano, trifluoromethyl, alkyl of 1 to 4 carbon atoms, alkoxy of 1 to 4 carbon atoms, or

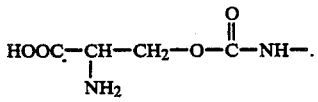

Preferred heteroaromatic acyl groups include those groups of the above formulas wherein $R_f$ is 2-amino-4-thiazolyl, 2-amino-5-halo-4-thiazolyl, 4-aminopyrimidin-2-yl, 5-amino-1,2,4-thiadiazol-3-yl, 2-thienyl, 2-furanyl, or 6-aminopyridin-2-yl.

(d) [[(4-Substituted-2,3-dioxo-1-piperazinyl)carbonyl]amino]arylacetyl groups having the formula

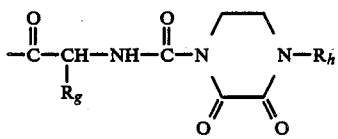

wherein $R_g$ is an aromatic group (including carbocyclic aromatics such as those of the formula

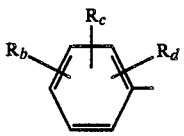

and heteroaromatics are included within the definition of $R_f$); and $R_h$ is alkyl, substituted alkyl (wherein the alkyl group is substituted with one or more halogen, cyano, nitro, amino or mercapto groups), arylmethyleneamino (i.e., $-N=CH-R_g$ wherein $R_g$ is as defined above), arylcarbonylamino (i.e.,

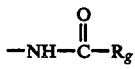

wherein $R_g$ is as defined above) or alkylcarbonylamino.

Preferred [[(4-substituted-2,3-dioxo-1-piperazinyl)-carbonyl]amino]arylacetyl groups include those wherein $R_h$ is ethyl, phenylmethyleneamino or 2-furylmethyleneamino.

(e) (Substituted oximino)arylacetyl groups having the formula

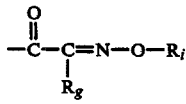

wherein $R_g$ is as defined above and $R_i$ is hydrogen, alkyl, cycloalkyl,

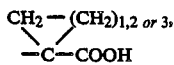

2-pyrrazolylmethyl, (2-oxo-3-pyrrolidinyl)methyl, alkylaminocarbonyl, arylaminocarbonyl (i.e.,

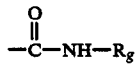

wherein $R_g$ is as defined above) or substituted alkyl (wherein the alkyl group is substituted with one or more halogen, cyano, nitro, amino, mercapto, alkylthio, aromatic group (as defined by $R_g$), carboxyl (including salts thereof), amido, alkoxycarbonyl, phenylmethoxycarbonyl, diphenylmethoxycarbonyl, hydroxyalkoxyphosphinyl, dihydroxyphosphinyl, hydroxy(phenylmethoxy)phosphinyl, dialkoxyphosphinyl or tetrazolyl substituents).

Preferred (substituted oxyimino)arylacetyl groups include those wherein $R_g$ is 2-amino-4-thiazolyl. Also preferred are those groups wherein $R_i$ is methyl, ethyl, carboxymethyl, 1-carboxy-1-methylethyl, 2,2,2-trifluoroethyl or 1-carboxycyclopropyl.

(f) (Acylamino)arylacetyl groups having the formula

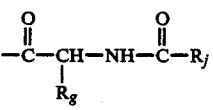

wherein $R_g$ is as defined above and $R_j$ is

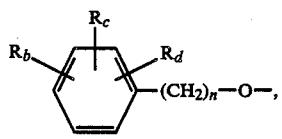

amino, alkylamino, (cyanoalkyl)amino, amido, alkylamido, (cyanoalkyl)amido,

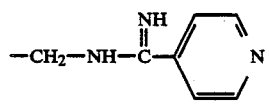

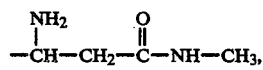

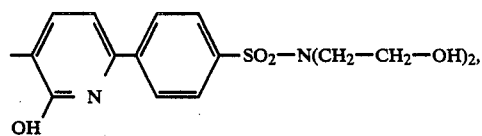

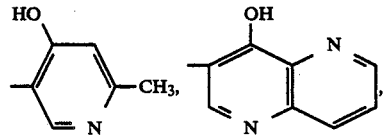

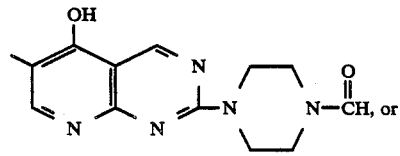

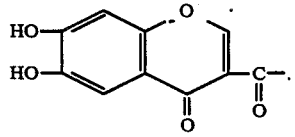

Preferred (acylamino)arylacetyl groups of the above formula include those groups wherein $R_j$ is amino or amido. Also preferred are those groups wherein $R_g$ is phenyl or 2-thienyl.

(g) [[[3-Substituted-2-oxo-1-imidazolidinyl]carbonyl-]amino]arylacetyl groups having the formula

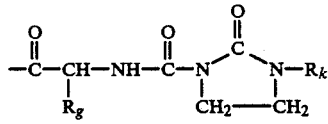

wherein $R_g$ is as defined above and $R_k$ is hydrogen, alkylsulfonyl, arylmethyleneamino (i.e., $-N=CH-R_g$ wherein $R_g$ is as defined above),

(wherein $R_m$ is hydrogen, alkyl or halogen substituted alkyl), aromatic group (as defined by $R_g$ above), alkyl or substituted alkyl (wherein the alkyl group is substituted with one or more halogen, cyano, nitro, amino or mercapto groups).

Preferred [[3-substituted-2-oxo-1-imidazolidinyl]carbonyl]amino]arylacetyl groups of the above formula include those wherein $R_g$ is phenyl or 2-thienyl. Also preferred are those groups wherein $R_k$ is hydrogen, methylsulfonyl, phenylmethyleneamino or 2-furylmethyleneamino.

The compounds of this invention form basic salts with various inorganic and organic bases which are also within the scope of this invention. Such salts include ammonium salts, alkali metal salts, alkaline earth metal salts, salts with organic bases, e.g., dicyclohexylamine, benzathine, N-methyl-D-glucamine, hydrabamine and the like. The pharmaceutically acceptable salts are preferred, although other salts are also useful, e.g., in isolating or purifying the product.

Some of the compounds of this invention may be crystallized or recrystallized from solvents containing water. In these cases, water of hydration may be formed. This invention contemplates stoichiometric hydrates as well as compounds containing variable amounts of water that may be produced by processes such as lyophilization.

The β-lactams of formula I contain at least one chiral center—the carbon atoms in the 3-position of the β-lactam nucleus to which the acylamino substituent ("$R_1-NH-$") is attached. This invention is directed to those β-lactams which have been described above, wherein the stereochemistry at the chiral center in the 3-position of the β-lactam nucleus is the same as the configuration at the carbon atom in the 6-position of naturally occurring penicillins (e.g., penicillin G) and as the configuration at the carbon atom in the 7-position of naturally occurring cephamycins (e.g., cephamycin C). Also included within the scope of this invention are racemic mixtures which contain the above-described β-lactams.

DETAILED DESCRIPTION OF THE INVENTION

The β-lactams of formula I, and pharmaceutically acceptable salts thereof, have activity against gram-positive and gram-negative organisms. The compounds of this invention can be used as agents to combat bacterial infections (including unirary tract infections and respiratory infections) in mammalian species, such as domesticated animals (e.g., dogs, cats, cows, horses, and the like) and humans.

For combating bacterial infections in mammals, a compound of this invention can be administered to a mammal in need thereof in an amount of about 1.4 mg/kg/day to about 350 mg/kg/day, preferably about 14 mg/kg/day to about 100 mg/kg/day. All modes of administration which have been used in the past to deliver penicillins and cephalosporins to the site of the infection are also contemplated for use with β-lactams of this invention. Such methods of administration include oral, intravenous, intramuscular, and as a suppository.

The β-lactams of formula I can be prepared from a 3-protected amino-2-azetidinone having the formula

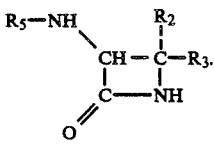

In formula II, and throughout the specification, the symbol "$R_5$" refers to an amino protecting group. These groups are well known in the field of β-lactam chemistry, and the particular group chosen is not critical. Benzyloxycarbonyl, trityl, and t-butoxycarbonyl are exemplary protecting groups. The reaction of a β-lactam of formula II with an isocyanate, having the formula

wherein Y is a leaving group such as chlorine, yields the corresponding compound having the formula

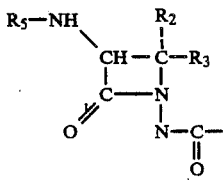

The reaction is preferably run in an inert organic solvent, e.g., ethyl acetate, tetrahydrofuran, dimethoxyethane, dichloromethane, acetonitrile or mixtures of these solvents. Displacement of the leaving group "Y" with the desired group can be accomplished using the appropriate nucleophile having the formula

optionally in the presence of a base (e.g., triethylamine), and yields the corresponding compound having the formula

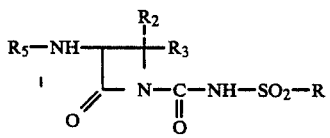

Alternatively, the displacement of the leaving group can be accomplished by reaction of a compound of formula IV with a protected form of a compound of formula V. Following the displacement reaction, the protecting groups can be removed using art-recognized techniques to yield a compound of formula VI. Still another procedure for displacing the leaving group comprises the reaction of a compound of formula IV with a trimethylsilyl derivative of a compound of formula V, optionally in the presence of a cation.

Protected forms of a compound of formula V containing a 3-hydroxy-4-pyrridone moiety, and of all reactants described herein which contain a 3-hydroxy-4-pyridone moiety, include those compounds wherein the hydroxyl group is protected, those compounds wherein the hydroxyl group and the ring nitrogen are protected, and those compounds wherein both pyridone oxygens are protected. Exemplary protecting groups are silyl (e.g., trimethylsilyl), benzyl and acyl (e.g., acetyl). If silyl is used, later deprotection can be accomplished using hydrolysis or fluoride mediated cleavage. If benzyl is used, later deprotection can be accomplished by hydrogenolysis. If acyl is used, later deprotection can be accomplished by hydrolysis.

Protected forms of a compound of formula V containing a catechol moiety, and of all reactants described herein which contain a catechol moiety, include those compounds wherein the hydroxyl groups are protected. Exemplary protecting groups are silyl (e.g., trimethylsilyl), benzyl and acyl (e.g., acetyl). If silyl is used, later deprotection can be accomplished using hydrolysis or fluoride mediated cleavage. If benzyl is used, later deprotection can be accomplished by hydrogenolysis. If acyl is used, later deprotection can be accomplished by hydrolysis.

Deprotection of a compound of formula VI using conventional techniques yields the corresponding key intermediate having the formula

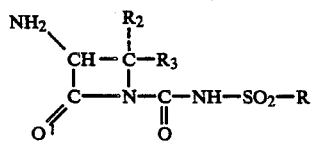

VII or a salt thereof. The particular deprotection reaction used will, of course, depend on the protecting group ("$R_5$") present. If, for example, $R_5$ is a t-butoxycarbonyl protecting group, deprotection can be accomplished by treatment of a compound of formula VI with acid (e.g., formic acid or trifluoroacetic acid). If, for example, $R_5$ is a benzyloxycarbonyl protecting group, deprotection can be accomplished by catalytic hydrogenation of a compound of formula VI. Alternatively, the $R_5$ protecting group can be removed simultaneously with the other pyridone or catechol protecting groups immediately following the above-described displacement reaction.

Well known acylation techniques can be used to convert an intermediate of formula VII to a corresponding product of formula I. Exemplary techniques include reaction of a compound of formula VII with a carboxylic acid ($R_1$—OH), or corresponding carboxylic acid halide or carboxylic acid anhydride. The reaction with a carboxylic acid proceeds most readily in the presence of a carbodiimide such as dicyclohexylcarbodiimide and a substance capable of forming an active ester in situ such as N-hydroxybenzotriazole. In those instances where the acyl group ($R_1$) contains reactive functionality (such as amino or carboxyl groups) it may be necessary to first protect those functional groups, then carry out the acylation reaction, and finally deprotect the resulting product.

An alternative procedure for preparing the compounds of formula I comprises first acylating (acylation techniques have been described above) a 3-amino-2-azetidinone having the formula

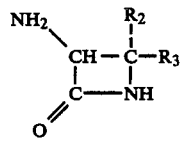

VIII to yield an intermediate having the formula

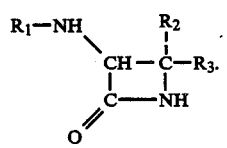

IX

The desired activating group can be introduced in the 1-position of a compound of formula IX (using the procedures described above) to obtain the corresponding product of formula I. In those instances wherein the acyl side-chain "$R_1$" contains reactive functionality (such as amino groups), it may be necessary to first protect those functional groups, then carry out the addition of the activating group in the 1-position, and finally deprotect the resulting product.

Still another synthesis for the preparation of compounds of formula I comprises the use of a 3-azido-2-azetidinone having the formula

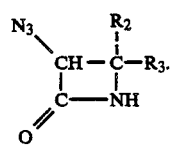

X

The desired activating group can be introduced in the 1-position of a compound of formula X (using the procedures described above) to obtain the corresponding compound having the formula

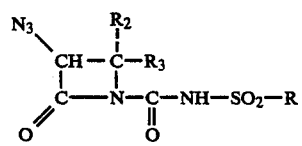

XI

Reduction of an intermediate of formula XI yields the corresponding intermediate having the formula

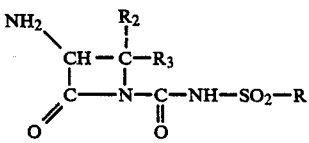

VII

The reduction can be accomplished by catalytic (e.g., palladium on charcoal or platinum oxide) hydrogenation or with reducing agents such as zinc or triphenylphosphine. As described above, from these key intermediates (compounds of formula VII), using conventional acylation techniques, it is possible to prepare the products of formula I.

Alternatively, a 3-azido-2-azetidinone of formula X can be reduced to the corresponding 3-amino-2-azetidinone having the formula

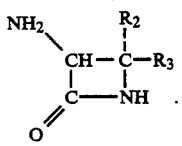    VIII

The reduction can be accomplished by catalytic (e.g., palladium on charcoal or platinum oxide) hydrogenation or with reducing agents such as zinc or triphenylphosphine. A 3-amino-2-azetidinone of formula VIII can be reacted as described above (i.e., first acylated and then treated as described above to introduce the desired activating group in the 1-position) to yield the products of formula I.

Still another synthesis for preparing the compounds of formula I wherein $R_2$ and $R_3$ are each hydrogen utilizes a 6-acylaminopenicillanic acid having the formula

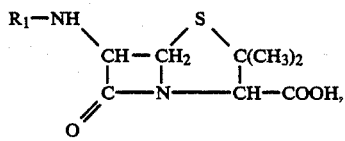    XII or a salt thereof, as the starting material. By adapting procedures described in the literature, 3-acylamino-2-azetidinone can be obtained from the corresponding 6-acylaminopenicillanic acid of formula XII; see, for example, *Chem. Soc. Special Publication* No. 28, pg. 288 (1977), *The Chemistry of Penicillins*, Princeton University Press, pg. 257, and *Synthesis*, 494 (1977).

As described in the literature 6-acylaminopenicillanic acid, or a salt thereof, can be desulfurized to yield a compound having the formula

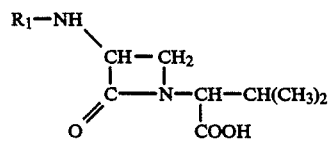    XIII by reduction using Raney nickel. The reaction can be run in water under reflux conditions.

Replacement of the carboxyl group of a compound of formula XIII with an acetate group followed by hydrolysis yields the corresponding 3-acylamino-2-azetidinone having the formula

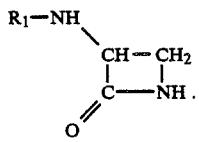    XIV

Treatment of a compound of formula XIII with cupric acetate and lead tetraacetate in an organic solvent (e.g., acetonitrile) replaces the carboxyl group with an acetate group. Hydrolysis of the resulting compound can be accomplished using potassium carbonate in the presence of sodium borohydride.

The desired activating group can be introduced in the 1-position of a compound of formula XIV (yielding products of formula I wherein $R_2$ and $R_3$ are each hydrogen) using the procedures described above.

Still another variation of the abovedescribed synthetic routes for preparing a compound of formula I wherein $R_2$ and $R_3$ are each hydrogen comprises first desulfurizing 6-aminopenicillanic acid, acylating the resulting compound to yield a compound of formula XIII and then proceeding as described above to obtain first a 3-acylamino-2-azetidinone of formula XIV and then a product of formula I.

The azetidinones of formula I can also be prepared from amino acids having the formula

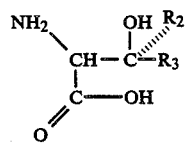    XV

The amino group is first protected (with a protecting group "$R_5$", e.g., t-butoxycarbonyl). The carboxyl group of the protected amino acid is then reacted with an amine having the formula

    XVI wherein Z is alkyl, benzyl or triphenylmethyl, in the presence of a carbodiimide to yield a compound having the formula

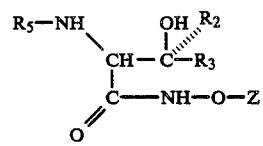    XVII

The hydroxyl group of a compound of formula XVII is converted to a leaving group ("OL") with a reagent, such as methanesulfonyl chloride or pyridine-$SO_3$ complex.

The fully protected compound having the formula

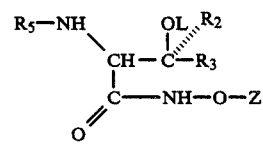    XVIII is cyclized by treatment with base, e.g., potassium carbonate. The reaction is preferably carried out in an organic solvent or an organic solvent/water mixture under reflux conditions, and yields a compound having the formula

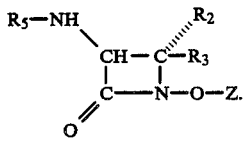   XIX

Alternatively, cyclization of a compound of formula XVII can be accomplished without first converting the hydroxyl group to a leaving group. Treatment of a compound of formula XVII with triphenylphosphine and diethylazodicarboxylate, yields a compound of formula XIX.

Exemplary procedures for the conversion of a compound of formula XVIII to a compound of formula XIX are described in *J. Amer. Chem. Soc.*, 102, 7026 (1980) and *J. Org. Chem.*, 47, 5160 (1982).

Both of the methods disclosed above for ring closure of a compound of formula XVII result in the inversion of the stereochemistry at the carbon atom bearing the $R_2$ and $R_3$ substituents when $R_2$ and $R_3$ are not the same.

Removal of the protecting group from the 1-position of an azetidinone of formula XIX can be accomplished via sodium reduction when Z is alkyl, and yields an intermediate having the formula

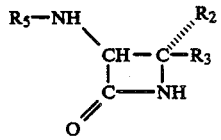   II (at least one of $R_2$ and $R_3$ is hydrogen). If Z is benzyl, catalytic (e.g., palladium on charcoal) hydrogenation will initially yield the corresponding N-hydroxy compound, which upon treatment with titanium trichloride yields an intermediate of formula II. If Z is triphenylmethyl, formic acid or 70% acetic acid/water will initially yield the corresponding N-hydroxy compound.

The desired activating group can be introduced in the 1-position of a compound of formula II using the procedures described above, and the resulting compound can be deprotected and acylated.

The nucleophiles of formula V wherein R is

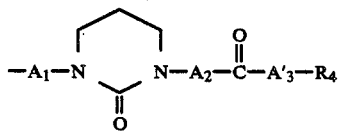

and $A_1$ and $A_2$ are each a single bond can be prepared by reacting a silylated derivative of tetrahydro-2(1H)-pyrimidinone

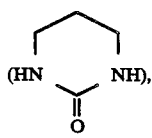

or the anion of tetrahydro-2(1H)-pyrimidinone formed with a strong non-nucleophillic base, with an activated, suitably protected derivative of an acid having the formula

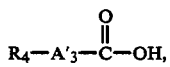   XX to obtain, upon deprotection, the corresponding compound having the formula

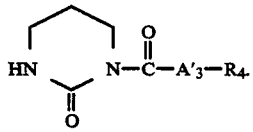   XXI

In the above formulas, and throughout the specification, the symbol $A_3'$ represents a single bond, —CH=CH—, —(CH$_2$)$_t$— or

wherein t is 1, 2, 3 or 4 (i.e., all $A_3$ groups other than —NH(CH$_2$)$_p$—). The reaction can be run in an inert organic solvent such as dimethylformamide, acetonitrile, dichloromethane, or tetrahydrofuran. The acid of formula XX can be activated with dicyclohexylcarbodiimide, or a combination of dicyclohexylcarbodiimide and hydroxybenzotriazole. An activated and suitably protected derivative of a compound of formula XX can also be the corresponding acid chloride (prepared with reagents such as phosphorus pentachloride, thionyl chloride, oxalyl chloride or triphenylphosphine/carbon tetrachloride) or a mixed anhydride (prepared with such reagents as diphenylphosphoryl chloride, pivaloyl chloride, or isobutyl chloroformate).

Protected forms of compounds of formula XX include those compounds wherein the hydroxyl groups are protected, if X is carboxyl, that group is protected, and if $A_3'$ is

the amino group is protected. Exemplary protecting groups are silyl, acetyl, benzyl, and methyl for the hydroxyl groups; benzyl, t-butyl and diphenylmethyl for the carboxy group; and t-butoxycarbonyl and benzyloxycarbonyl for the amino group. Methodology used for deprotecting a compound of formula XXI will depend on the protecting group used: hydrolysis removes silyl and acetyl groups; hydrogenolysis removes benzyl and benzyloxycarbonyl groups; aqueous hydrobromic acid at elevated temperature or boron tribromide removes methyl groups; and trifluoroacetic acid removes t-butoxycarbonyl groups.

The compound of formula XX wherein $R_4$ is a 3-hydroxy-4-pyridone moiety and $A_3'$ is a single bond can be prepared as described in the literature; see *Helv. Chem. Acta*, 43, 469 (1960) and *J. Med. Chem.*, 17, 1 (1974).

The compounds of formula XX wherein $R_4$ is a dihydroxyphenyl moiety and $A_3'$ is a single bond, —(CH$_2$-

)$_t$— wherein t is 1 or 2 or —CH=CH— are commercially available.

The compound of formula XX wherein R$_4$ is 3-hydroxy-4-pyridone and A$_3$' is —CH=CH— can be formed by oxidizing

    XXII (suitably protected) to the corresponding aldehyde having the formula

    XXIII (suitably protected), reacting the aldehyde with a carboxyl protected derivative

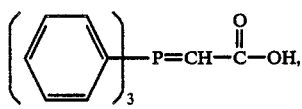    XXIV and deprotecting to yield

    XXV

The compounds of formula XX wherein A$_3$' is —(CH$_2$)$_t$— and t is 2, 3 or 4 can be formed by conjugation of a compound of formula XXIII (suitably protected) with a Wittig reagent having the formula

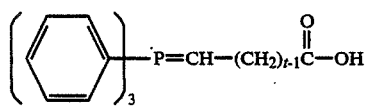    XXVI (suitably protected at the carboxyl group), subsequent hydrogenation of the resulting exocyclic double bond, and deprotection to yield

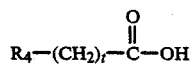    XXVII wherein t is 2, 3 or 4.

The compounds of formula XX wherein R$_4$ is a 3-hydroxy-4-pyridone moiety and A$_3$' is —(CH$_2$)$_t$— and t is 1 can be formed by reaction of a suitably protected compound having the formula

    XXVIII (wherein L$_a$ is a leaving group such as chloride, bromide, methanesulfonyloxy or toluenesulfonyloxy), with cyanide and subsequent hydrolysis and deprotection to yield the compound of formula XXVII wherein T is 1. A compound of formula XXVIII can be prepared from a compound of formula XXII (suitably protected) by methods familiar in the art (such as reaction with thionyl chloride or methanesulfonylchloride/triethylamine).

The compounds of formula XX wherein R$_4$ is a 3-hydroxy-4-pyridone moiety and A$_3$' is

can be prepared from a compound of formula XXIII (suitably protected) by methods familiar in the art such as a Strecker synthesis.

Alternatively, a compound of formula XXIII can be reacted with trimethylsilylcyanide, followed by treatment with an acid to yield

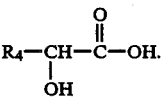    XXIX

Reaction of a compound of formula XXIX with thionylbromide followed by sodium azide and then reduction yields the corresponding acid

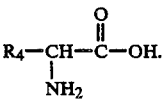    XXX

The compounds of formula XX wherein R$_4$ is a dihydroxyphenyl moiety and A$_3$' is

can be prepared as described on the literature; see, for example, Physiol. Chemie, 98: 226 (1917) and German Offenlegungsschrift 2,151,521.

The nucleophiles of formula V wherein R is

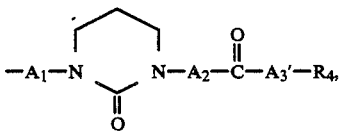

A$_1$ is a single bond and A$_2$ is —NH— can be prepared by reacting an activated and optionally protected derivative of a compound of formula XX with 3-amino-tetrahydro-2(1H)-pyrimidinone

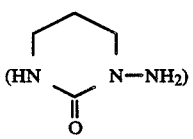

to yield upon deprotection

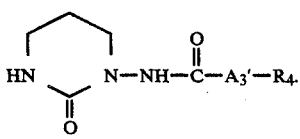

The reaction can be run in an inert solvent such as dimethylformamide. The acid of formula XX can be activated with a mixture of dicyclohexylcarbodiimide, N-hydroxybenzotriazole and 4-dimethylaminopyridine.

The nucleophiles of formula V wherein R is

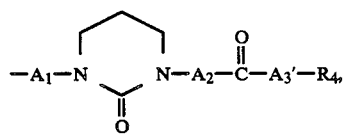

$A_1$ is a single bond and $A_2$ is —$CH_2$—$CH_2$—NH— can be prepared by reacting an activated and optionally protected derivative of a compound of formula XX with 3-(2-aminoethyl)-tetrahydro-2(1H)-pyrimidinone

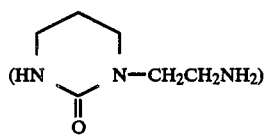

to yield upon deprotection

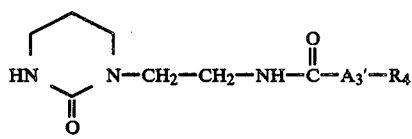

XXXII

The nucleophiles of formula V wherein R is

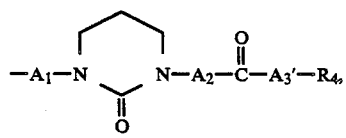

$A_1$ is a single bond and $A_2$ is

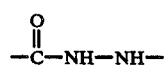

can be prepared by reacting

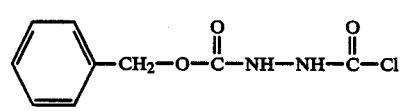

XXXIII with a silylated form of tetrahydro-2(1H)-pyrimidinone, the anion of tetrahydro-2(1H)-pyrimidinone formed with a strong non-nucleophilic base, or with tetrahydro-2(1H)-pyrimidinone in the presence of an organic base to yield

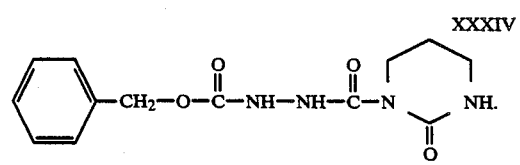

XXXIV

Catalytic hydrogenation of the compound of formula XXXIV yields the compound having the formula

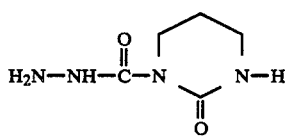

XXXV which can be coupled with an activated and optionally protected derivative of a compound of formula XX to yield, upon deprotection,

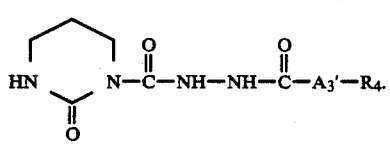

XXXVI

Alternatively, the compound of formula XXXV can be prepared by first reacting 3-chlorocarbonyltetrahydro-2(1H)pyrimidinone with t-butoxycarbonyl protected hydrazone to yield

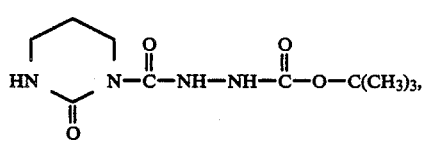

XXXVII and deprotecting the compound of formula XXXVII.

The nucleophiles of formula V wherein R is

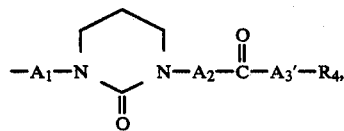

$A_1$ is

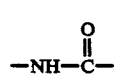

and $A_2$ is a single bond can be prepared by reacting a compound having the formula

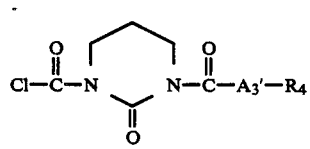

XXXVIII (suitably protected) with hexamethyldisilazane to yield upon hydrolysis and deprotection a compound having the formula

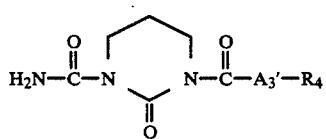 XXXIX

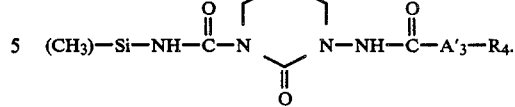 XLIII

The compounds of formula XXXVIII (suitably protected) can be prepared by reacting a silylated form of a compound of formula XXI (optionally protected) with phosgene.

Alternatively, a compound of formula XXXIX can be prepared by reacting a protected form of a compound of formula XXI with chlorosulfonyl isocyanate followed by hydrolysis of the resulting intermediate and cleavage of the protecting groups.

The nucleophiles of formula V wherein R is

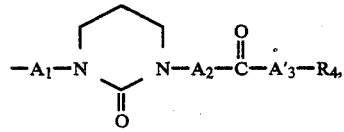 XL $A_1$ is

and $A_2$ is —NH— can be prepared by reacting a silylated form of the compound

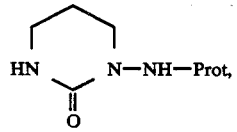 XL wherein the symbol Prot can be an amino protecting group such as t-butoxycarbonyl or benzyloxycarbonyl, with phosgene to yield

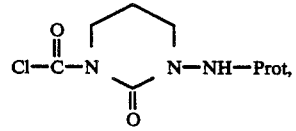 XLI which can be reacted with hexamethyldisilazane to yield

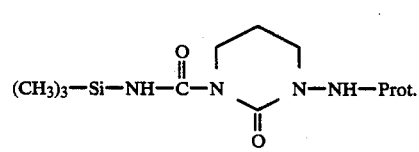 XLII

Cleavage of the non-silyl amino protecting group followed by reaction with an optionally protected activated form of a compound of formula XX yields A non-silylated derivative of a compound of formula XLIII can be prepared by coupling an activated form of a compound of formula XX (optionally protected) with a compound having the formula

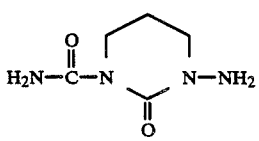 XLIV to yield

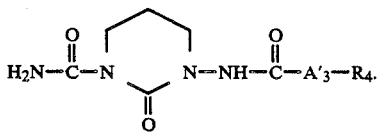 XLV

A salt of the compound of formula XLIV can be prepared by reacting the compound of the formula

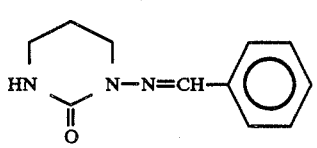 XLVI with chlorosulfonylisocyanate followed by mild hydrolysis of the reaction product to yield a compound of the formula

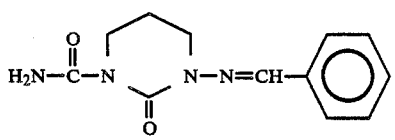 XLVII which, on further hydrolysis, e.g., by reflux with dilute aqueous acid yields the salt of the compound of formula XLIV.

Alternatively, the compound of formula XLIV can be prepared by reacting a compound of formula XL with chlorosulfonyl isocyanate to yield upon hydrolysis the compound having the formula

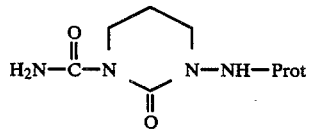 XLVIII which can be deprotected to yield XLIV.

The nucleophiles of formula V wherein R is

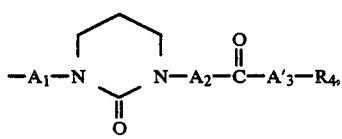

$A_1$ is

and $A_2$ is —$CH_2$—$CH_2$—NH— can be prepared by first deprotecting 1-(aminocarbonyl-3-[2-[[(t-butoxy)carbonyl]amino]-ethyl]-tetrahydro-2(1H)-pyrimidinone and coupling the resulting compound with an activated form of a compound of formula XX (optionally protected) to obtain after deprotection

XLIX

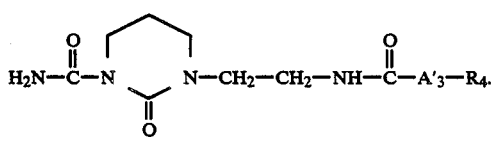

The nucleophiles of formula V wherein R is

XL

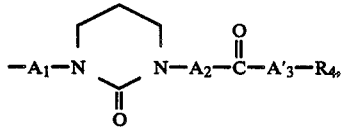

$A_1$ is

and $A_2$ is

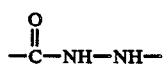

can be prepared by reacting a silylated form of a compound of formula XXXVI (optionally protected) with phosgene followed by hexamethyldisilazane to yield upon hydrolysis and deprotection

L

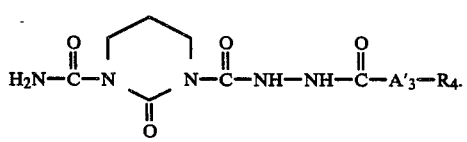

Alternatively, a compound of formula L can be prepared by reacting a protected form of a compound of formula XXXVI with chlorosulfonylisocyanate followed by hydrolysis of the resulting intermediate and cleavage of the protecting groups. Alternatively, compound XXXIV can be reacted with chlorosulfonyl isocyanate followed by hydrolysis of the resulting intermediate to yield

LI

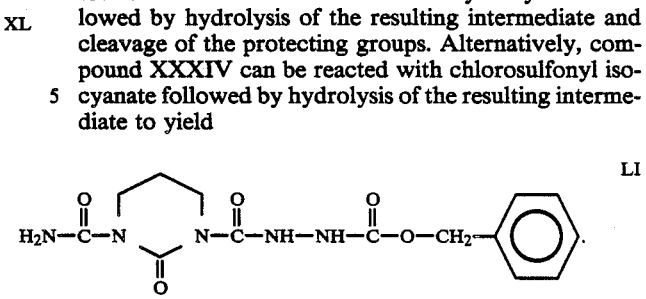

Deprotection of LI by hydrogenolysis yields

LII

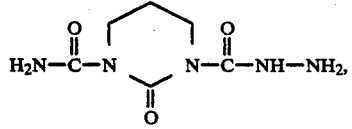

which can be coupled with an activated and optionally protected derivative of a compound of formula XX to yield upon deprotection a compound of formula L.

The nucleophiles of formula V wherein R is

XL

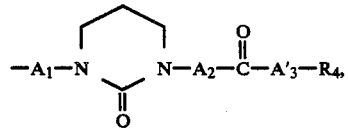

$A_1$ is —NH— and $A_2$ is a single bond can be prepared by coupling the compound of formula XL to an activated form of a compound of formula XX (optionally protected) and cleaving the protecting group to yield

LIII

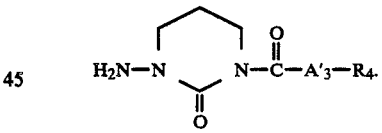

The nucleophiles of formula V wherein R is

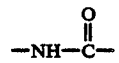

$A_1$ is —NH— and $A_2$ is —NH— can be prepared by coupling a monoprotected (preferably with t-butoxycarbonyl or benzyloxycarbonyl) derivative of 1,3-diamino-tetrahydro-2(1H)-pyrimidinone with an activated form of a compound of formula XX (optionally protected) and deprotecting the resulting compound to yield

LIV

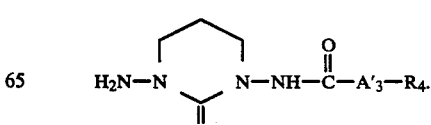

Alternatively, a compound of formula LIV can be formed by nitrosating a protected form of a compound of formula XXXI followed by reduction of the nitroso group and cleavage of the protecting groups.

The nucleophiles of formula V wherein R is

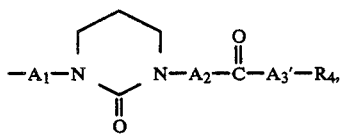

$A_1$ is —NH— and $A_2$ is —CH$_2$—CH$_2$—NH— can be prepared by nitrosating a compound of formula XXXII (suitably protected) to yield a compound having the formula

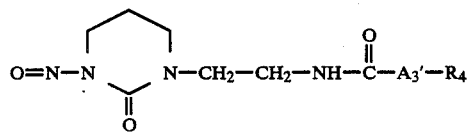

LV (suitably protected) and reducing and deprotecting that compound to yield

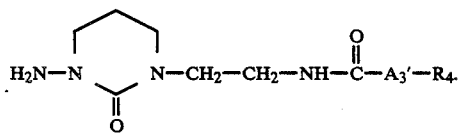

LVI

The nucleophiles of formula V wherein R is

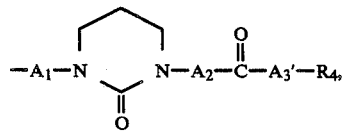

$A_1$ is —NH— and $A_2$ is

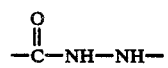

can be prepared by nitrosating, reducing and deprotecting a protected derivative of a compound of formula XXXVI. The resulting compound has the formula

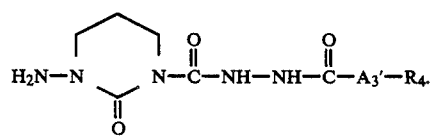

LVII

Alternatively, a compound of formula LVII can be prepared by reacting a compound of formula XL with phosgene to yield

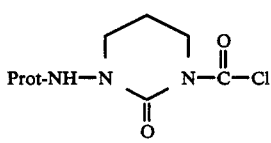

LVIII which, on reaction with a monoprotected hydrazine in the presence of base, yields

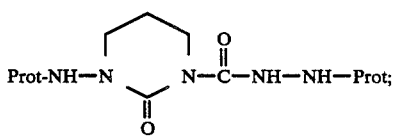

LIX (The two protecting groups must be different). Selective removal of the hydrazine protecting group yields

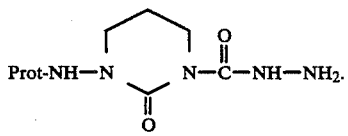

LX

Coupling of a compound of formula LX with an activated optionally protected form of a compound of formula XX, followed by deprotection, yields a compound of formula LVII.

The nucleophiles of formula V wherein R is

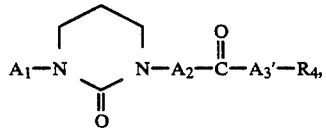

$A_1$ is

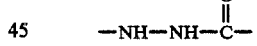

and $A_2$ is a single bond can be prepared by reacting a compound of formula XXXVIII (preferably a protected derivative thereof) with hydrazine (preferably in monoprotected form) in the presence of a base or with a silylated form of hydrazine or monoprotected hydrazine to yield a protected derivative of

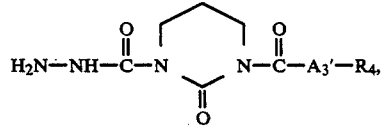

LXI which can be deprotected using conventional techniques.

Alternatively, a compound of formula XXXVII (either a silylated derivative thereof or an anion thereof formed by reaction with a strong base) can be reacted with an activated form of formula XX (suitably protected) and deprotected to yield a compound of formula LXI.

The nucleophiles of formula V wherein R is

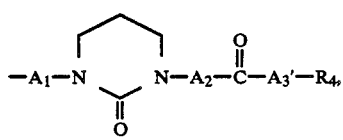

A₁ is

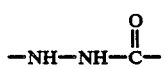

and A₂ is —NH— can be prepared by selective removal of the non-hydrazine protecting group of a compound of formula LIX, followed by coupling with an activated optionally protected compound of formula XX and subsequent deprotection to yield a compound having the formula

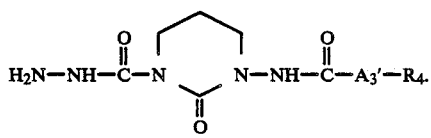

LXII

The nucleophiles of formula V wherein R is

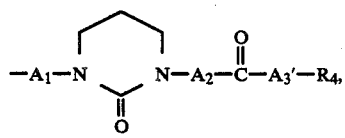

A₁ is

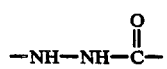

and and A₂ is —CH₂—CH₂—NH— can be prepared by sequentially reacting a compound of formula XXXII (or a protected derivative thereof) with phosgene followed by hydrazine (or a monoprotected derivative thereof) in the presence of a silylating agent such as N-methyl-N-(trimethylsilyl)trifluoroacetamide to yield upon deprotection

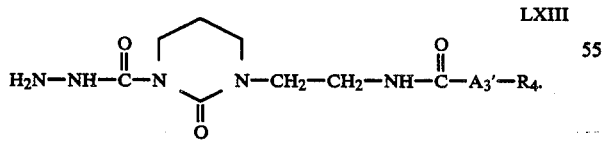

LXIII

Alternatively, an amino protected derivative of 1-(2-aminoethyl)-2-imidazolidinone (optionally silylated) can be reacted with phosgene, and then with a monoprotected derivative of hydrazine in the presence of a base or a silylating agent (e.g., N-methyl-N-(trimethylsilyl)trifluoroacetamide or bis(trimethylsilyl)acetamide) to yield a protected derivative of the compound having the formula

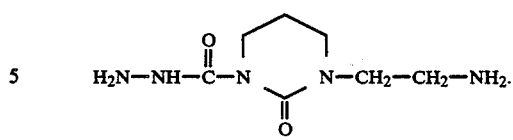

LXIV

The groups used to protect the terminal amino groups in a compound of formula LXIV should have been chosen so that the protecting group on the aminoethyl group can be selectively removed. The resulting mono-deprotected compound can be coupled with an activated form of an acid of formula XX (or a protected derivative thereof) to yield (after deprotection) a compound of formula LXIII.

The nucleophiles of formula V wherein R is

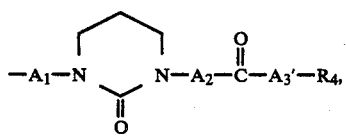

A₁ is

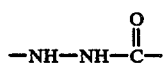

and A₂ is

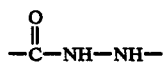

can be prepared by reacting the compound of formula XXXIV (optionally as a silylated derivative thereof) with phosgene to yield a protected derivative of the compound having the formula

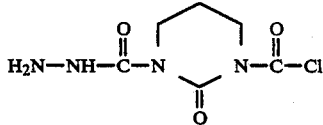

LXV which can be coupled with a protected derivative of hydrazine to yield a protected derivative of

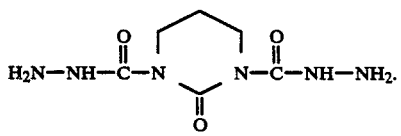

LXVI

The groups used to protect the terminal amino groups in a compound of formula LXVI should be chosen so that one of the protecting groups can be selectively removed. The resulting mono-deprotected compound can be coupled with an optionally protected activated form of an acid of formula XX to yield (after deprotection) a compound having the formula

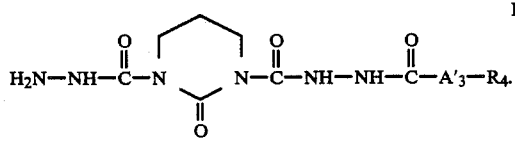 LXVII

The nucleophiles of formula V wherein R is

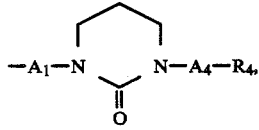

$A_1$ is a single bond and $A_4$ is a single bond or $CH_2$ can be prepared by reacting an optionally protective derivative of a compound having the formula $NH_2$—$(CH_2)_p$—$R_4$ (p is 0 or 1)  LXVIII with a 3-(chloropropyl)isocyanate to yield the compound having the formula

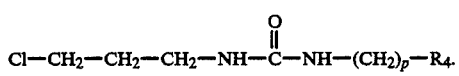 LXIX

Treatment of LXIX with base yields the compound having the formula

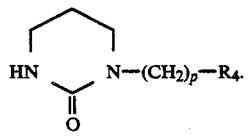 LXX

The nucleophiles of formula V wherein R is

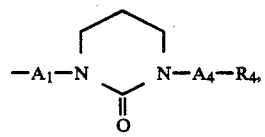

$A_1$ is a single bond and $A_4$ is —N=CH— or —NH—CH$_2$— can be prepared by condensing 3-amino-tetrahydro-2(1H)-pyrimidinone with the aldehyde having the formula XXIII (optionally protected) to yield (after deprotection) the compound having the formula

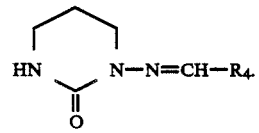 LXXI

Reduction of the compound of formula LXXI (optionally protected) by catalytic hydrogenation or using sodium cyanoborohydride yields the compound having the formula

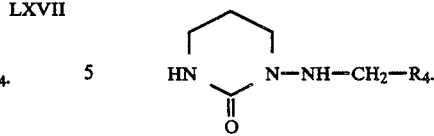 LXXII

The nucleophiles of formula V wherein R is

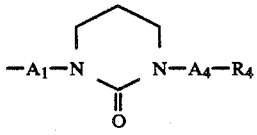

and $A_1$ is

can be prepared by reacting a suitably protected derivative of a compound of formula LXX, LXXI or LXXII with phosgene to yield a protected derivative of the formula

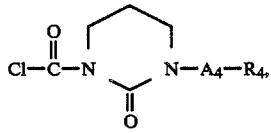 LXXIII which can be reacted with hexamethyldisilazane to yield upon deprotection and hydrolysis

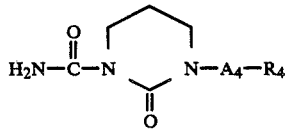 LXXIV

Alternatively, nucleophiles of formula V wherein R is

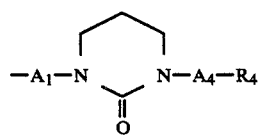

and $A_1$ is

can be prepared by reacting a suitably protected derivative of a compound of formula LXX, LXXI or LXXII with chlorosulfonyl isocyanate to yield upon hydrolysis and deprotection a compound of formula LXXIV.

The nucleophiles of formula V wherein R is

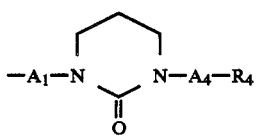

and $A_1$ is —NH— can be prepared by nitrosating a suitably protected derivative of a compound of formula LXX, LXXI or LXXII (with, for example, nitrous acid), reducing the resulting compound (using, for example, zinc under acidic conditions) and deprotecting to yield

LXXV

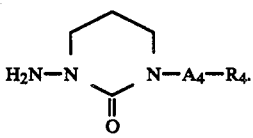

Alternatively, those compounds of formula LXXV wherein $A_4$ is —N=CH— or —NH—CH$_2$— can be prepared by reacting monoprotected 1,3-diaminotetrahydro-2(1H)-pyrimidinone with a compound of formula XXIII (or a protected derivative thereof) and deprotecting the product to yield the derivative of formula LXXV wherein $A_4$ is —N=CH—. Reduction of that derivative yields the compound of formula LXXV wherein $A_4$ is —NH—CH$_2$—.

The nucleophiles of formula V wherein R is

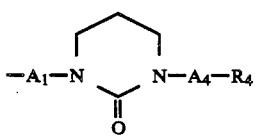

and $A_1$ is

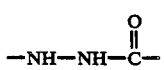

can be prepared by reacting a compound of formula LXXIII (suitably protected) with a monoprotected hydrazine in the presence of a base or a silylating agent. The products, after deprotection, have the formula

LXXVI

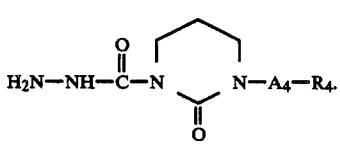

A compound having the formula

LXXVII

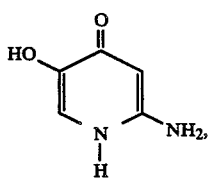

can be prepared by converting a protected form of the compound having the formula

LXXVIII

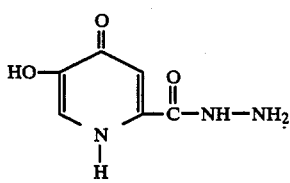

to a protected form of the compound of formula LXXVII by the procedure of K. Heyns et al., *Chem. Ber.*, 87, 1440 (1954), followed by deprotection to yield the compound of formula LXXVII, per se.

A compound of formula LXXVIII can be prepared from a suitably protected form of a compound of the formula

LXXIX

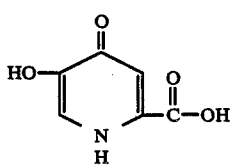

by conversion to an ester (such as ethyl or methyl), reaction with hydrazine and deprotection. Alternatively, a suitably protected, activated form of a compound of formula LXXIX can be reacted with a monoprotected hydrazine to yield upon deprotection a compound of formula LXXVIII.

Alternatively, a protected form of the compound of formula LXXVII can be prepared by reacting a suitably protected form of a compound of formula LXXIX with diphenylphosphoryl azide in the presence of a base, e.g. triethylamine.

A compound having the formula

NH$_2$—CH$_2$—R$_4$    LXXX can be prepared from a compound of formula XXVIII (suitably protected) by treatment with azide, reduction of the azide and deprotection.

The nucleophiles of formula V wherein R is

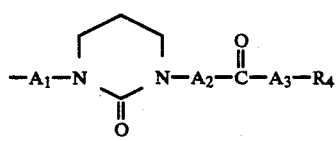

and $A_3$ is —NH—(CH$_2$)$_p$— can be prepared by reacting an optionally protected compound of the formula

LXXXI

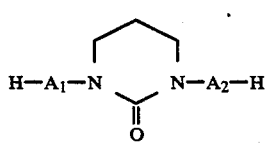

with an isocyanate of the formula

O=C=N—(CH$_2$)$_p$—R$_4$    LXXXII to yield, after deprotection, a compound of the formula

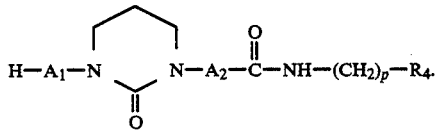
LXXXIII

Alternatively, a compound of formula LXXXI optionally protected, can be reacted with phosgene to yield a compound of the formula

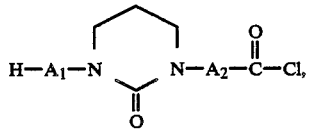
LXXXIV which on treatment with a compound of formula LXVIII yields a compound of formula LXXXIII.

Alternatively, the nucleophiles of formula V wherein R is

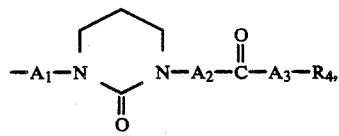

$A_1$ is

or

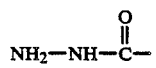

and $A_3$ is —NH—$(CH_2)_p$— can be prepared by reacting a compound of the formula

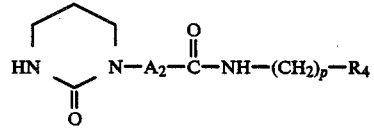
LXXXV (optionally silylated) with phosgene to yield a compound of the formula

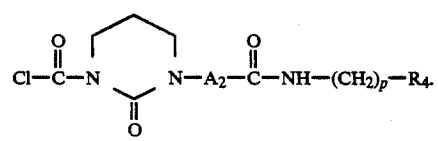
LXXXVI

A compound of formula LXXXVI can be reacted with hexamethyldisilazane followed by hydrolysis of the remaining silyl group on the nitrogen to yield the corresponding compound having the formula

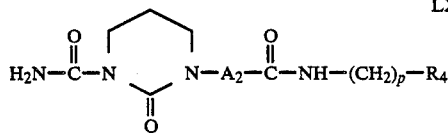
LXXXVII or with monoprotected hydrazine to yield, after deprotection,

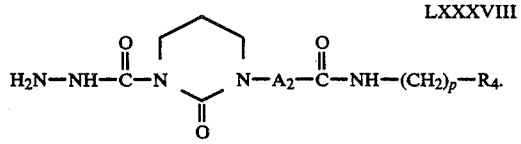
LXXXVIII

The compounds of formula I wherein R is

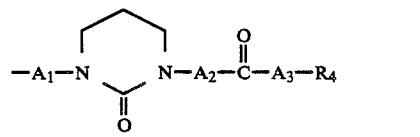

are preferred. Most preferred are those compounds of formula I wherein R is

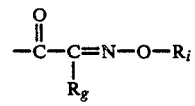

Also preferred are those compounds of formula I wherein $R_1$ is

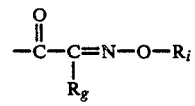

and $R_g$ is 2-amino-4-thiazolyl and $R_i$ is methyl, ethyl, carboxymethyl, 1-carboxyl-1-methylethyl, 1-carboxy-1-ethyl or

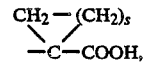

wherein s is 1, 2 or 3. The use of these preferred $R_1$ acyl groups yields a product which exists as the syn or anti isomer or as a mixture of isomers. The syn isomer exhibits greater activity than the anti isomer.

The following examples are specific embodiments of this invention.

EXAMPLE 1

[3S(Z)]-2-[[[1-(2-Amino-4-thiazolyl)-2-[[1-[[[[3-[[(1,4-dihydro-5-hydroxy-4-oxo-2-pyridinyl)carbonyl]amino]-tetrahydro-2-oxo-1(2H)-pyrimidinyl]sulfonyl]amino]-carbonyl]-2-oxo-3-azetidinyl]amino]-2-oxoethylidene]amino]oxy]-2-methylpropanoic acid, disodium salt

(A) Tetrahydro-2(1H)-pyrimidinone

A mixture of 50 g (674 mmol) 1,3-diaminopropane and 79.7 g (674 mmol) diethylcarbonate was heated overnight in steel autoclave at 180° C. The resulting white crystals were filtered off, washed with ether and dried in vacuo. Yield 55.5 g of the desired product, melting point 265.1° C.

(B) Tetrahydro-3-[(phenylmethylene)amino]-2(1H)-pyrimidinone

To a suspension of 20 g (199 mmol) tetrahydro-2(1H)-pyrimidinone in a mixture of 480 ml water and 48 ml concentrated sulfuric acid was added at 0° C. 13.8 g (199 mmol) sodium nitrite. After stirring for 1.5 hours, 26.12 g (399 mmol) zinc was added in portions. The mixture was stirred for 20 minutes at 0° C. and for an additional hour at room temperature. The solids were filtered off and after the addition of 19 g (179 mml) benzaldehyde the mixture was stirred overnight at room temperature. The desired product was filtered off, washed with water and dried in vacuo. Yield 17.9 g, melting point 189.7° C.

(C) 3-Aminotetrahydro-2(1H)-pyrimidinone, monohydrochloride

A solution of 5.7 g (28.0 mmol) tetrahydro-3-[(phenylmethylene)amino]-2(1H)-pyrimidinone in a mixture of 43 ml water and 43 ml concentrated hydrochloric acid was steam distilled until no additional benzaldehyde condensed. The residual solution was evaporated to dryness, triturated with ethanol and dried in vacuo. Yield 3.07 g, melting point 210°-215° C.

(D) 1,4-Dihydro-4-oxo-5-(phenylmethoxy)-N-(tetrahydro-2-oxo-1-(2H)-pyrimidinyl)-2-pyridinecarboxamide To a solution of 4.7 g. (19.2 mmol) 1,4-dihydro-4-oxo-5-(phenylmethoxy)-2-pyridinecarboxylic acid in 50 ml N,N-dimethylformamide was added 4.74 g (23 mmol) dicyclohexylcarbodiimide and 0.29 g (1.92 mmol) N-hydroxybenzotriazole. The mixture was stirred for 1 hour. To this was added a solution of 2.85 g (19.2 mmol) 3-aminotetrahydro-2(1H)-pyrimidinone, monohydrochloride and 1.94 g (19.2 mmol) triethylamine in 30 ml N,N-dimethylformamide. After stirring overnight the dicyclohexylurea was filtered off and the N,N-dimethylformamide evaporated in vacuo. The residue was triturated with ether to yield 8.47 g of the desired product (contained dicyclohexylurea). This crude material was used in the next step without further purification.

(E) 1,4-Dihydro-5-hydroxy-4-oxo-N-(tetrahydro-2-oxo-1(2H)-pyrimidinyl)-2-pyridinecarboxamide To a suspension of 1.71 g. (ca. 5 mmol) crude 1,4-dihydro-4-oxo-5-(phenylmethoxy)-N-(tetrahydro-2-oxo-1(2H)-pyrimidinyl)-2-pyridine-carboxamide in 22 ml acetonitrile was added 4.1 g (20 mmol) bis(trimethyl-silyl)acetamide. After stirring for 20 minutes the undissolved dicyclohexylurea was filtered off and 0.85 g palladium on carbon were added to the filtrate. After the mixture had been hydrogenated for one hour, the catalyst was removed by filtration and 2.1 ml methanol and 0.1 ml acetic acid were added to the filtrate. After stirring overnight the desired product was filtered off and dried in vacuo. Yield 0.7 g, melting point 285°-290° C. (dec.).

(F) (S)-[1-[[[[3-[[(1,4-Dihydro-5-hydroxy-4-oxo-2-pyridinyl)carbonyl]amino]tetrahydro-2-oxo-1(2H)-pyrimidinyl]sulfonyl]amino]carbonyl]-2-oxo-3-azetidinyl]carbamic acid, phenylmethyl ester 2.73 g (10.82 mmol) 1,4-dihydro-5-hydroxy-4-oxo-N-(tetrahydro-2-oxo-1(2H)-pyrimidinyl)-2-pyridinecarboxamide and 8.63 g (43.29 mmol) N-methyl-N-trimethylsilyltrifluoroacetamide were dissolved in ethyl acetate and stirred for 1 hour (solution A). To a suspension of 2.38 g (10.82 mmol) (S)-(2-oxo-3-azetidinyl)carbamic acid, phenylmethyl ester in 80 ml ethyl acetate was added 1.53 g (10.82 mmol) chlorosulfonyl isocyanate. After stirring for 1 hour, the solution was cooled to 0° C. and 9 ml dichloromethane and subsequently solution A were added. After stirring overnight at room temperature ice water was added and the pH was adjusted to 1.3 with 3N hydrochloric acid. The precipitate was filtered off, washed with water, dried in vacuo and slurried with ether. Yield 4.95 g, melting range 150°-230° C. (dec.).

(G) (S)-N-[3-[[[(3-Amino-2-oxo-1-azetidinyl)carbonyl]amino]-sulfonyl]tetrahydro-2-oxo-1(2H)-pyrimidinyl]-1,4-dihydro-5-hydroxy-4-oxo-2-pyridinecarboxamide, inner salt 4.95 g (8.57 mmol) (S)-[1-[[[[3-[[(1,4-dihydro-5-hydroxy-4-oxo-2-pyridinyl)-carbonyl]amino]tetrahydro-2-oxo-1(2H)-pyrimidinyl]sulfonyl]amino]carbonyl]-2-oxo-3-azetidinyl]carbamic acid, phenylmethyl ester was dissolved in 50 ml N,N-dimethylformamide. After the addition of 2.5 g palladium on carbon, the mixture was hydrogenated for 1 hour. The catalyst was removed and subsequently the filtrate added dropwise to 500 ml isopropanol. The desired product was filtered off, slurried with either and dried in vacuo. Yield 3.03 g, melting range 160°-220° C. (dec.).

(H) (S)-2-[[[1-(2-Amino-4-thiazolyl)-2-[[1-[[[[3-[[(1,4-dihydro-5-hydroxy-4-oxo-2-pyridinyl)carbonyl]amino]tetrahydro-2-oxo-1(2H)-pyrimidinyl]sulfonyl]amino]carbonyl]-2-oxo-3-azetidinyl]amino-2-oxoethylidene]amino]oxy]-2-methylpropanoic acid, diphenylmethyl ester To a solution of 1.87 g (4.26 mmol) (Z)-2-amino-α-[[2-(diphenylmethoxy)-1,1-dimethyl-2-oxoethoxy]imino]-4-thiazoleacetic acid in 100 ml N,N-dimethylformamide were added at −30° 1.29 g (12.8 mmol) triethylamine and 1.02 g (4.26 mmol) diphenyl chlorophosphate. After stirring for 1 hour, 0.43 g (4.26 mmol) triethylamine and 1.89 g (4.26 mmol) (S)-N-[3-[[[(3-amino-2-oxo-1-azetidinyl)carbonyl]amino]-sulfonyl]tetrahydro-2-oxo-1(2H)-pyrimidinyl]-1,4-dihydro-5-hydroxy-4-oxo-2-pyridinecarboxamide, inner salt were added. After stirring for 2 hours at −10° C. and 1.5 hours at 0° C., the N,N-dimethylformamide was evaporated in vacuo, and to the residue were added ice water and ethyl acetate. The pH was adjusted to 1.0 with 3N hydrochloric acid. The insoluble residue was filtered off, washed with water and dried in vacuo. Yield 2.58 g.

(I)

[3S(Z)]-2-[[[1-(2-Amino-4-thiazolyl)-2-[[1-[[[[3-[[1,4--dihydro-5-hydroxy-4-oxo-2-pyridinyl)carbonyl]amino]-tetrahydro-2-oxo-1(2H)-pyrimidinyl]sulfonyl]amino]-carbonyl]-2-oxo-3-azetidinyl]amino]-2-oxoethylidene]amino]oxy]-2-methylpropanoic acid, disodium salt To a suspension of 2.52 g (2.91 mmol) (S) -2-[[[1-(2-amino-4-thiazolyl)-2-[[1-[[[[3-[[1,4-dihydro-5-hydroxy-4-oxo-2-pyridinyl)carbonyl]amino]tetrahydro-2-oxo-1(2H)-pyrimidinyl]sulfonyl]amino]carbonyl]-2-oxo-3-azetidinyl]amino]-2-oxoethylidene]amino]oxy]-2-methylpropanoic acid, diphenylmethyl ester in 4.4 ml anisole was added dropwise at −10° C. 22 ml trifluoroacetic acid. After stirring for 1 hour 100 ml ether was added and the resulting precipitate was filtered off after stirring for an additional 30 minutes. This material was dissolved in 50 ml water and the pH brought to 6.5 with 1N sodium hydroxide. Freeze drying yielded 2.86 g crude salt which was chromatographed on XAD under MPLC conditions with water as eluent. Yield of pure freeze dried product 0.16 g, melting point 250°–275° C.

EXAMPLE 2

[3S(Z)]-2-[[[1-(2-Amino-4-thiazolyl)-2-[[1-[[[[[3-[[(1,4--dihydro-5-hydroxy-4-oxo-2-pyridinyl)carbonyl]amino]tetrahydro-2-oxo-1(2H)-pyrimidinyl]carbonyl]amino]sulfonyl]amino]carbonyl]-2-oxo-3-azetidinyl]amino]-2-oxoethylidene]amino]oxy]-2-methylpropanoic acid, disodium salt (A) (Tetrahydro-2-oxo-1(2H)-pyrimidinyl)carbamic acid, phenylmethyl ester 3-Aminotetrahydro-2(1H)-pyrimidinone, monohydrochloride (30 g, 0.198 mol) was dissolved in a mixture of 240 ml water and 200 ml tetrahydrofuran. The pH was adjusted to 8.5 and benzylchloroformate (33.8 g, 0.198 mmol) was added dropwise while keeping the pH between 8 and 9. After the pH remained constant, the mixture was stirred for an additional hour. The tetrahydrofuran was removed in vacuo and the resulting crystals were filtered off with suction, triturated with ether and dried in vacuo. Yield 35.6 g, melting point 161°–163° C.

(B)
Tetrahydro-2-oxo-3-[[(phenylmethoxy)carbonyl]amino]-1(2H)-pyrimidinecarboxamide To a suspension of (tetrahydro-2-oxo-1(2H)-pyrimidinyl)carbamic acid, phenylmethyl ester (35.5 g, 135.9 mmol) in 500 ml ethyl acetate, chlorosulfonyl isocyanate (24.0 g, 169.9 mmol) was added. The resulting solution was stirred for one hour and hydrolyzed by adding 175 ml water. The phases were separated, the organic phase washed with water and brine and dried over magnesium sulfate. Evaporation of the solvent and trituration of the residue with ether yielded 38.0 g of the desired product, melting point 135.6° C.

(C)
3-Aminotetrahydro-2-oxo-1(2H)-pyrimidinecarboxamide

Tetrahydro-2-oxo-3-[[(phenylmethoxy)carbonyl]amino]-1(2H)-pyrimidinecarboxamide (37.45 g. 128.1 mmol), dissolved in 650 ml N,N-dimethylformamide, was hydrogenated over 15 g palladium on activated carbon for 2 hours. The catalyst was removed by filtration and the solvent evaporated in vacuo. Trituration with ether furnished 20.1 g of the desired product, melting point 153°–156° C.

(D)
3-[[[4,5-Bis(phenylmethoxy)-2-pyridinyl]carbonyl]amino]-tetrahydro-2-oxo-1(2H)-pyrimidinecarboxamide To a solution of 3-aminotetrahydro-2-oxo-1(2H)-pyrimidinecarboxamide (10 g, 63.2 mmol) in 350 ml N,N-dimethylformamide were added dicyclohexylcarbodiimide (15.7 g, 75.9 mmol), N-hydroxybenzotriazole (0.97 g, 6.32 mmol) and 4,5-bis(phenylmethoxy)-2-pyridinecarboxylic acid (21.2 g, 63.2 mmol) and the mixture was stirred overnight at room temperature. Dicyclohexylurea (13.6 g) was filtered off and the solvent was removed in vacuo. Trituration of the residue with ether gave 27.5 g of the desired product, melting point 192°–195° C.

(E)
3-[[(1,4-Dihydro-5-hydroxy-4-oxo-2-pyridinyl)carbonyl]-amino]tetrahydro-2-oxo-1(2H)-pyrimidinecarboxamide 3-[[[4,5-bis(phenylmethoxy)-2-pyridinyl]carbonyl]amino]-tetrahydro-2-oxo-1(2H)-pyrimidinecarboxamide (27.45 g, 57.7 mmol), dissolved in 750 ml N,N-dimethylformamide, was hydrogenated for 1.5 hours over 10 g palladium on activated carbon. The catalyst was removed by filtration and the solvent distilled off in vacuo. The residue was triturated twice with ether to give two batches (15.5 g and 4.0 g) of the desired product, melting point 215°–220° C.

(F)
(S)-[1-[[[[[[3-[[(1,4-Dihydro-5-hydroxy-4-oxo-2-pyridinyl)-carbonyl]amino]tetrahydro-2-oxo-1(2H)-pyrimidinyl]carbonyl]amino]-sulfonyl]amino]carbonyl]-2-oxo-3-azetidinyl]carbamic acid, phenylmethyl ester To a suspension of (S)-(2-oxo-3-azetidinyl)carbamic acid, phenylmethyl ester (6.61 g, 30.0 mmol) in 300 ml ethyl acetate chlorosulfonyl isocyanate (4.25 g, 30.0 mmol) was added, and the mixture was stirred for 1 hour at room temperature (solution A). To a solution of 3-[[(1,4-dihydro-5-hydroxy-4-oxo-2-pyridinyl)-carbonyl]-amino]tetrahydro-2-oxo-1(2H)-pyrimidinecarboxamide (8.86 g, 30.0 mmol) in 300 ml ethyl acetate, N-methyl-N-trimethylsilyltrifluoroacetamide (23.91 g, 120 mmol) was added. After 30 minutes a clear solution was obtained; 300 ml dichloromethane was added, followed by the dropwise addition of solution A at 0° C. After stirring overnight at room temperature 300 ml water was added whereupon an oily residue separated. The solvents were decanted off and the residue triturated with ether to give 10.27 g of the desired product (crude). The product was suspended in water and the pH adjusted to 6 with 2N sodium hydroxide. After freeze drying of the resulting solution the product was

(G)
[3S(Z)]-2-[[[1-(2-Amino-4-thiazolyl)-2-[[1-[[[[[3-[[(1,-4-dihydro-5-hydroxy-4-oxo-2-pyridinyl)carbonyl-]amino]tetrahydro-2-oxo-1(2H)-pyrimidinyl]carbonyl-]amino]sulfonyl]amino]carbonyl]-2-oxo-3-azetidinyl-]amino]-2-oxoethylidene]amino]oxy]-2-methyl-propanoic acid, diphenylmethyl ester To a solution of (S)-[1-[[[[[[3-[[(1,4-dihydro-5-hydroxy-4-oxo-2-pyridinyl)-carbonyl]amino]tetrahydro-2-oxo-1(2H)-pyrimidinyl]-carbonyl]amino]sulfonyl-]amino]carbonyl]-2-oxo-3-azetidinyl]-carbamic acid, phenylmethyl ester (5.24 g, 8.44 mmol) in 250 ml N,N-dimethylformamide, N-methyl-N-trimethylsilyl trifluoroacetamide (8.41 g, 42.2 mmol) was added. After 30 minutes 1.8 g palladium on carbon were added and the mixture was hydrogenolyzed for 1 hour. The catalyst was removed by filtration and to the filtrate (Z)-2-amino-α-[[2-(diphenylmethoxy)-1,1-dimethyl-2-oxoethoxy]imino]-4-thiazoleacetic acid, 1H-benzotriazol-1-yl ester (4.22 g, 7.59 mmol) was added. After stirring overnight the solvent was distilled off and the residue triturated with 100 ml water. The resulting solid was filtered off with suction and dried in vacuo. Yield 6.14 g.

(H)
[3S(Z)]-2-[[[1-(2-Amino-4-thiazolyl)-2-[[1-[[[[-[3-[[(1,-,4-dihydro-5-hydroxy-4-oxo-2-pyridinyl)-carbonyl-]amino]tetrahydro-2-oxo-1(2H)-pyrimidinyl]carbonyl-]amino]sulfonyl]amino]carbonyl]-2-oxo-3-azetidinyl-]amino]-2-oxoethylidene]amino]-oxy]-2-methyl-propanoic acid, disodium salt To a suspension of [3S(Z)]-2-[[[1-(2-amino-4-thiazolyl)-2-[[1-[[[[[3-[[(1,4-dihydro-5-hydroxy-4-oxo-2-pyridinyl)carbonyl]-amino]tetrahydro-2-oxo-1(2H)-pyrimidinyl]carbonyl]amino]sulfonyl]amino]carbonyl]-2-oxo-3-azetidinyl]amino]-2-oxoethylidene]amino]oxy]-2-methylpropanoic acid, diphenylmethyl ester (6.1 g, 6.72 mmol) in 6.5 ml anisole, 65 ml trifluoroacetic acid was added dropwise at 0° C. After stirring for 1 hour the volatiles were distilled off in vacuo and the oily residue was triturated with ether to give a solid which was filtered off, washed with ether and dried in vacuo. The salt was suspended in water and the pH brought to 6 with 2N sodium hydroxide. Freeze drying yielded 8.60 g of the crude product which was chromatographed in seven portions on Organogen with water as eluent to give, after freeze drying, a total amount of 2.5 g of the desired product. A second chromatography yielded 0.66 g of the desired product, melting point >300° C.

What is claimed is:
1. A compound having the formula

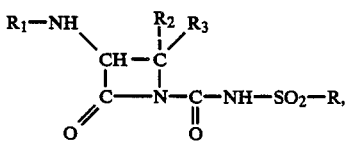

or a pharmaceutically acceptable salt thereof, wherein R is

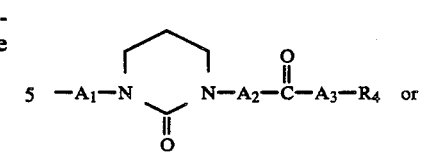

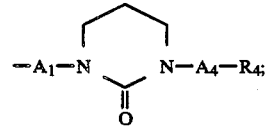

or $R_1$ is an acyl group derived from a carboxylic acid;

$R_2$ and $R_3$ are the same or different and each is hydrogen, alkyl, alkenyl, alkynyl, cycloalkyl, phenyl, substituted phenyl or a 4, 5, 6 or 7-membered heterocycle or one of $R_2$ and $R_3$ is hydrogen and the other is azido, halomethyl, dihalomethyl, trihalomethyl, alkoxycarbonyl, 2-phenylethenyl, 2-phenylethynyl, carboxyl,

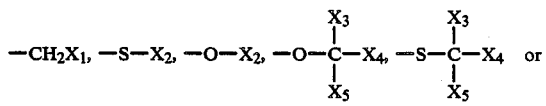

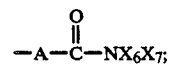

$X_1$ is azido, amino, hydroxy, carboxyl, alkoxycarbonyl, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano,

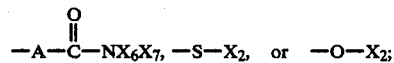

$X_2$ is alkyl, substituted alkyl, phenyl, substituted phenyl, phenylalkyl, (substituted phenyl)alkyl, alkanoyl, phenylalkanoyl, (substituted phenyl)alkanoyl, phenylcarbonyl, (substituted phenyl)carbonyl, or heteroarylcarbonyl;

one of $X_3$ and $X_4$ is hydrogen and the other is hydrogen or alkyl, or $X_3$ and $X_4$ when taken together with the carbon atom to which they are attached from a cycloalkyl group;

$X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl, (substituted amino)carbonyl, or cyano;

$X_6$ and $X_7$ are the same or different and each is hydrogen, alkyl, phenyl or substituted phenyl, or $X_6$ is hydrogen and $X_7$ is amino, substituted amino, alkanoylamino or alkoxy, or $X_6$ and $X_7$ when taken together with the nitrogen atom which they are attached form a 4, 5, 6 or 7-membered heterocycle;

A is —CH=CH—, —(CH$_2$)$_m$—, —(CH$_2$)$_m$—O—, —(CH$_2$)$_m$—NH— or —CH$_2$—S—CH$_2$—;

m is 0, 1 or 2;

$R_4$ is

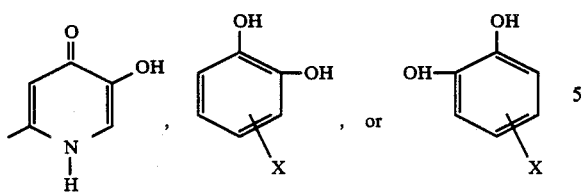

wherein X is hydrogen, halogen, carboxyl, sulfo, carbamoyl, aminosulfonyl, cyano, alkyl, alkanoyl; or alkoxycarbonyl;

$A_1$ is a single bond,

—NH— or

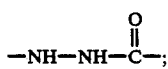

$A_2$ is a single bond, —NH—, —CH$_2$—CH$_2$—NH—, or

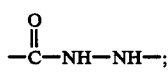

$A_3$ is a single bond, —CH=CH—, '(CH$_2$)$_t$—, —NH—(CH$_2$)$_p$— or

wherein t is 1, 2, 3 or 4 and p is 0 or 1; and $A_4$ is a single bond, —CH$_2$—, —NH—CH$_2$—, or —N=CH—;

wherein the term "substituted phenyl" refers to a phenyl group substituted with 1, 2 or 3 amino, halogen, hydroxyl, trifluoromethyl, alkyl of 1 or 4 carbon atoms, alkoxy of 1 to 4 carbon atoms, alkanoyloxy aminocarbonyl, or carboxy groups;

the term "substituted amino" refers to a group having the formula —NX$_8$X$_9$ wherein X$_8$ is hydrogen, alkyl, phenyl, substituted phenyl, phenylalkyl or (substituted phenyl)alkyl, and X$_9$ is alkyl, phenyl, substituted phenyl, phenylalkyl, (substituted phenyl)alkyl, hydroxy, cyano, alkoxy, phenylalkoxy or amino;

the term "heteroaryl" refers to pyridinyl, furanyl, pyrrolyl, thienyl, 1,2,3-triazolyl, 1,2,4-triazolyl, imdazolyl, thiazolyl, thiadiazolyl, pyrimidinyl, oxazolyl, triazinyl, tetrazolyl or one of the above groups substituted with one or more halogen, hydroxy, nitro, amino, cyano, trifluoromethyl, alkyl of 1 to 4 carbons, alkoxy of 1 to 4 carbons, alkylsulfonyl, phenyl, substituted phenyl, 2-furfurylideneamino, benzylideneamino, or substituted alkyl wherein the alkyl group has 1 to 4 carbons, groups;

the term "a 4, 5, 6, or 7-membered heterocycle" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, teterazolyl azetidinyl, oxetanyl, thietanyl, piperidinyl, piperazinyl, imidazolylidinyl, oxazolidinyl, pyrrolidinyl, tetrahydropyrimidinyl, dihydrothiazolyl or hexahydroazepinyl or one of the above groups substituted with one or more oxo, halogen, hydroxy, nitro, amino, cyano, trifluoromethyl, alkyl of 1 to 4 carbons, alkoxy of 1 to 4 carbons, alkylsulfonyl, phenyl, substituted phenyl, 2-furfurylideneamino, benzylideneamino, or substituted alkyl wherein the alkyl group has 1 to 4 carbons, groups;

the term "substituted alkyl" refers to alkyl groups substituted with one or more azido, amino (—NH$_2$), halogen, hydroxy, carboxy, cyano, alkoxycarbonyl, aminocarbonyl, alkanoyloxy, alkoxy, phenyloxy, (substituted phenyl)oxy, mercapto, alkylthio, phenylthio, (substituted phenyl)thio, alkylsulfinyl, or alkylsulfonyl groups.

2. A compound in accordance with claim 1 wherein R is

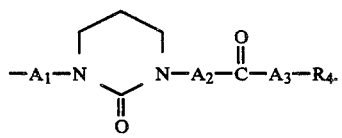

3. A compound in accordance with claim 1 wherein R is

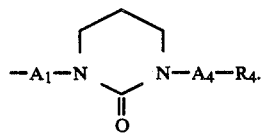

4. A compound in accordance with claim 1 wherein R$_4$ is

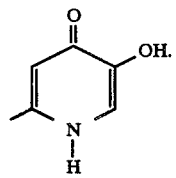

5. A compound in accordance with claim 1 wherein R$_4$ is

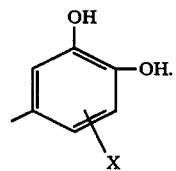

6. A compound in accordance with claim 1 wherein R$_4$ is

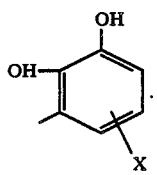

7. A compound in accordance with claim 1 wherein $R_2$ and $R_3$ are each hydrogen.

8. A compound in accordance with claim 1 wherein R is

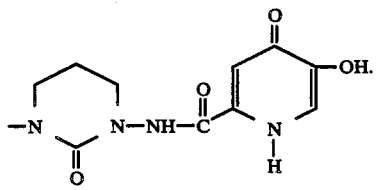

9. A compound in accordance with claim 1 wherein $R_1$ is

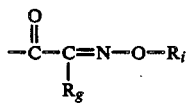

and $R_g$ is 2-amino-4-thiazolyl and $R_i$ is methyl, ethyl, carboxymethyl, 1-carboxy-1-methylethyl, 1-carboxy-1-ethyl, or

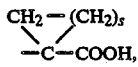

wherein s is 1, 2 or 3.

10. A compound in accordance with claim 1 wherein $R_1$ is

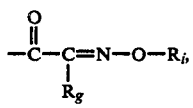

$R_g$ is 2-amino-4-thiazolyl and $R_i$ is carboxymethyl, 1-carboxy-1-methylethyl, 1-carboxy-1-ethyl, or

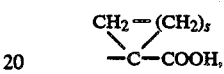

wherein s is 1, 2 or 3.

11. The compound in accordance with claim 1, [3S(Z)]-2-[[[1-(2-amino-4-thiazolyl)-2-[[1-[[[[3-[[(1,4-dihydro-5-hydroxy-4-oxo-2-pyridinyl)carbonyl]amino]tetrahydro-2-oxo-1(2H)-pyrimidinyl]sulfonyl]amino]carbonyl]-2-oxo-3-azetidinyl]amino]-2-oxoethylidene]amino]oxy]-2-methylpropanoic acid or a pharmaceutically acceptable salt thereof.

12. The compound in accordance with claim 1, [3S(Z)]-2-[[[1-(2-amino-4-thiazolyl)-2-[[1-[[[[[3-[[(1,4-dihydro-5-hydroxy-4-oxo-2-pyridinyl)carbonyl]amino]tetrahydro-2-oxo-1(2H)-pyrimidinyl]carbonyl]amino]sulfonyl]amino]carbonyl]-2-oxo-3-azetidinyl]amino]-2-oxoethylidene]amino]oxy]-2-methylpropanoic acid, or a pharmaceutically acceptable salt thereof.

* * * * *